United States Patent
McIntyre et al.

(10) Patent No.: US 9,675,810 B2
(45) Date of Patent: Jun. 13, 2017

(54) DEFIBRILLATOR ELECTRODE IDENTIFICATION SYSTEM

(71) Applicant: HeartSine Technologies Limited, Belfast (GB)

(72) Inventors: Allister Robert McIntyre, Newtownards Co Down (GB); Johnny Houston Anderson, Holywood Co Down (GB)

(73) Assignee: Heartsine Technologies Limited, Belfast (GB)

( * ) Notice: Subject to any disclaimer, the term of this patent is extended or adjusted under 35 U.S.C. 154(b) by 156 days.

(21) Appl. No.: 14/179,125

(22) Filed: Feb. 12, 2014

(65) Prior Publication Data
US 2014/0228903 A1 Aug. 14, 2014

(30) Foreign Application Priority Data
Feb. 14, 2013 (GB) .................................. 1302625.7

(51) Int. Cl.
*A61N 1/00* (2006.01)
*A61N 1/39* (2006.01)

(52) U.S. Cl.
CPC .......... *A61N 1/3925* (2013.01); *A61N 1/3931* (2013.01)

(58) Field of Classification Search
CPC ........ A61N 1/046; A61N 1/0563; A61N 1/39; A61N 1/3925; A61N 1/3931;
(Continued)

(56) References Cited

U.S. PATENT DOCUMENTS 4,695,107 A * 9/1987 Leppert .................. H01R 23/72
439/389
5,441,520 A * 8/1995 Olsen .................... A61N 1/3931
607/115
(Continued)

*Primary Examiner* — Mallika D Fairchild

(57) ABSTRACT

An electrode identification system (1) for defibrillators, comprising an electrode plug (2) adapted for connection to at least one electrode having a first pair of conducting contacts (6, 8), an identification element (10) connected between the first pair of conducting contacts, a second pair of conducting contacts (12, 14) for connection to the electrode, and a housing (16) providing a cavity (18, 20) which substantially encases the first and second pairs of conducting contacts and the identification element and an aperture through which ends of the first and second pairs of conducting contacts extend, a defibrillator socket (3) adapted for connection to a defibrillator and adapted for connection to an electrode plug having a first pair of conducting contacts (24, 26) for connection to the first pair of conducting contacts of the electrode plug, a second pair of conducting contacts (28, 30) for connection to the second pair of conducting contacts of the electrode plug and for connection to the defibrillator, and a housing (32) providing a cavity (34, 36) which substantially encases the first and second pairs of conducting contacts and an aperture through which ends of the first and second pairs of conducting contacts extend, and an electrode identification unit (4) adapted for connection to a defibrillator socket having a circuit comprising contacts for connection to the first pair of conducting contacts of the electrode plug via the first pair of conducting contacts of the defibrillator socket, a signal detector (42) connected to the circuit which detects a signal from the identification element of the electrode plug, and a processor (44) which uses a measure of the signal to determine an identification characteristic of the identification element of the electrode plug and from this identifies a category of the electrode connected to the electrode plug.

25 Claims, 2 Drawing Sheets

Figure 1:
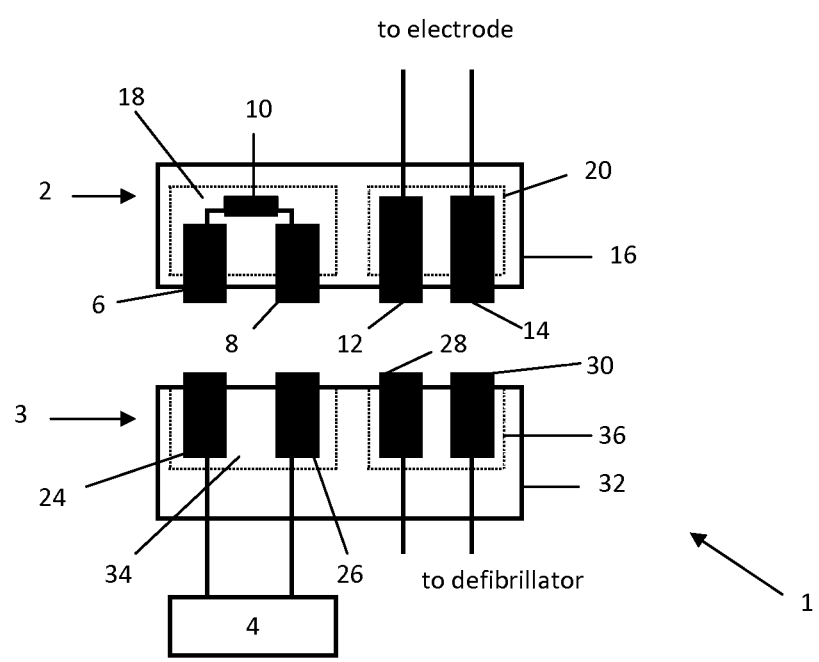

(58) Field of Classification Search
CPC ...... A61B 2019/448; A61B 2019/4873; A61B 2018/00178; A61B 2018/00988
See application file for complete search history.

(56) References Cited

U.S. PATENT DOCUMENTS

| | | | | |
|---|---|---|---|---|
| 6,101,413 | A * | 8/2000 | Olson | A61N 1/046 607/5 |
| 7,689,278 | B2 * | 3/2010 | Jonsen | A61B 19/026 607/5 |
| 2009/0065565 | A1 * | 3/2009 | Cao | A61B 18/1402 235/375 |
| 2009/0099423 | A1 * | 4/2009 | Al-Ali | H01R 13/6275 600/300 |

* cited by examiner

DEFIBRILLATOR ELECTRODE IDENTIFICATION SYSTEM

The invention relates to identification systems for defibrillator electrodes.

Portable defibrillators, such as those for use in public areas, on aircraft etc., comprise two main parts—a housing enclosing defibrillation generation and control circuitry etc. and electrodes for application to a subject to provide defibrillation pulses measure ECG signals, etc. The electrodes are designed to be separable from the defibrillator housing and to be connected thereto by electrode wires and an electrode plug. It is necessary to provide different categories of electrodes having different properties for a defibrillator, for example electrodes that are suitable for delivering defibrillation signals to adults, electrodes that are suitable for delivering defibrillation signals to children, electrodes that are used for measuring ECG signals, electrodes having a required size, shape, etc. It is critical that in each of various different circumstances of use of a defibrillator, electrodes from an appropriate category having the correct properties are used. It is therefore preferable to provide a mechanism for identifying the category of electrodes connected to the defibrillator.

According to the present invention there is provided an electrode identification system for defibrillators, comprising:

an electrode plug adapted for connection to at least one electrode having:
  a first pair of conducting contacts,
  an identification element connected between the first pair of conducting contacts,
  a second pair of conducting contacts for connection to the electrode, and
  a housing providing a cavity which substantially encases the first and second pairs of conducting contacts and the identification element and an aperture through which ends of the first and second pairs of conducting contacts extend,
a defibrillator socket adapted for connection to a defibrillator and adapted for connection to an electrode plug having:
  a first pair of conducting contacts for connection to the first pair of conducting contacts of the electrode plug,
  a second pair of conducting contacts for connection to the second pair of conducting contacts of the electrode plug and for connection to the defibrillator, and
  a housing providing a cavity which substantially encases the first and second pairs of conducting contacts and an aperture through which ends of the first and second pairs of conducting contacts extend, and
an electrode identification unit adapted for connection to a defibrillator socket having:
  a circuit comprising contacts for connection to the first pair of conducting contacts of the electrode plug via the first pair of conducting contacts of the defibrillator socket,
  a signal detector connected to the circuit which detects a signal from the identification element of the electrode plug, and
  a processor which uses a measure of the signal to determine an identification characteristic of the identification element of the electrode plug and from this identifies a category of the electrode connected to the electrode plug.

The defibrillator plug may be adapted for connection to a plurality of different categories of electrodes. The different categories of the different electrodes may each be associated with a different value or a different range of values of identification characteristic of the identification elements of the electrode plugs connected to the electrodes. The different values or ranges of values of identification characteristics of the identification elements of the different electrode plugs may have separations which are greater than a measurement accuracy of the electrode identification unit. The categories of the electrodes may comprise any of a category of electrode for use with a child, a category of electrode for use with an adult, a category of electrode for measuring an ECG signal and not for delivering defibrillation signals, a category of size of the electrode, a category of shape of the electrode, a category of manufacture date of the electrode, a category of lot number of the electrode, a category of construction of the electrode, for example a gel electrode.

The identification element may comprise a resistive identification element. The identification characteristic of the resistive identification element may comprise a value or a range of values of resistance of the resistive identification element. The identification element may comprise a capacitive identification element. The identification characteristic of the capacitive identification element may comprise a value or a range of values of capacitance of the capacitive identification element. The identification element may comprise an inductive identification element. The identification characteristic of the inductive identification element may comprise a value or a range of values of inductance of the inductive identification element.

The electrode plug may be connected to at least one electrode in the course of manufacture of the electrode. Thus appropriate electrode plugs and electrodes may be used together.

The first and second pairs of conducting contacts of the electrode plug may comprise pins and may be elongate and may comprise a conductive element, such as any of copper, gold, nickel, tin or any combination thereof.

The housing of the electrode plug may be substantially rigid and may be comprised of a non conductive plastic material, such as any of ABS, polycarbonate, compressed polystyrene or any combination thereof. The housing of the electrode plug may be provided with a location device which attaches to the defibrillator socket such that the first pair of conducting contacts of the electrode plug connect with the first pair of conducting contacts of the defibrillator socket, and the second pair of conducting contacts of the electrode plug connect with the second pair of conducting contacts of the defibrillator socket.

The housing of the electrode plug may provide a cavity divided into separate first and second portions. The first portion may substantially encase the first pair of conducting contacts and the identification element and the second portion may substantially encase the second pair of conducting contacts to electrically insulate the first pair of conducting contacts and the identification element from the second pair of conducting contacts. The first pair of conducting contacts and the identification element may be moulded or otherwise inserted into the housing providing the first portion of the cavity. The second pair of conducting contacts may be moulded or otherwise inserted into the housing providing the second portion of the cavity.

The defibrillator socket may be connected to a defibrillator by being provided as an integral part of the defibrillator. The defibrillator socket may be removably connected to a defibrillator via a socket receiver provided on the defibrillator.

The first and second pair of conducting contacts of the defibrillator socket may comprise pins and may be elongate and may comprise a conductive element, such as any of copper, gold, nickel, tin or any combination thereof.

The first pair of conducting contacts of the defibrillator socket may be connected to the first pair of conducting contacts of the electrode plug by contact between the pairs of contacts. The second pair of conducting contacts of the defibrillator socket may be connected to the second pair of conducting contacts of the electrode plug by contact between the pairs of contacts.

The housing of the defibrillator socket may be substantially rigid and may be comprised of a non conductive plastic material, such as any of ABS, polycarbonate, compressed polystyrene or any combination thereof. The housing of the defibrillator socket may be provided with a location device which attaches to the electrode plug such that the first pair of conducting contacts of the electrode plug connect with the first pair of conducting contacts of the defibrillator socket, and the second pair of conducting contacts of the electrode plug connect with the second pair of conducting contacts of the defibrillator socket.

The housing of the defibrillator socket may provide a cavity divided into separate first and second portions. The first portion may substantially encase the first pair of conducting contacts and the second portion may substantially encase the second pair of conducting contacts to electrically insulate the first and second pairs of conducting contacts from each other. The first pair of conducting contacts may be moulded or otherwise inserted into the housing providing the first portion of the cavity. The second pair of conducting contacts may be moulded or otherwise inserted into the housing providing the second portion of the cavity.

The circuit of the electrode identification unit may comprise a voltage divider circuit. The voltage divider circuit may comprise a voltage generator and an electrical impedance element. The voltage divider circuit may be connected to the first pair of conducting contacts of the electrode plug via the first pair of conducting contacts of the defibrillator socket in an arrangement which divides the voltage of the voltage generator between the identification element of the electrode plug and the electrical impedance element of the voltage divider circuit. The signal detector may be connected to the voltage divider circuit to detect a signal in the circuit. The processor may use the signal or a measure of the signal to determine the identification characteristic of the identification element of the electrode plug and from this identify the category of the electrode connected to the electrode plug.

Figure 2:
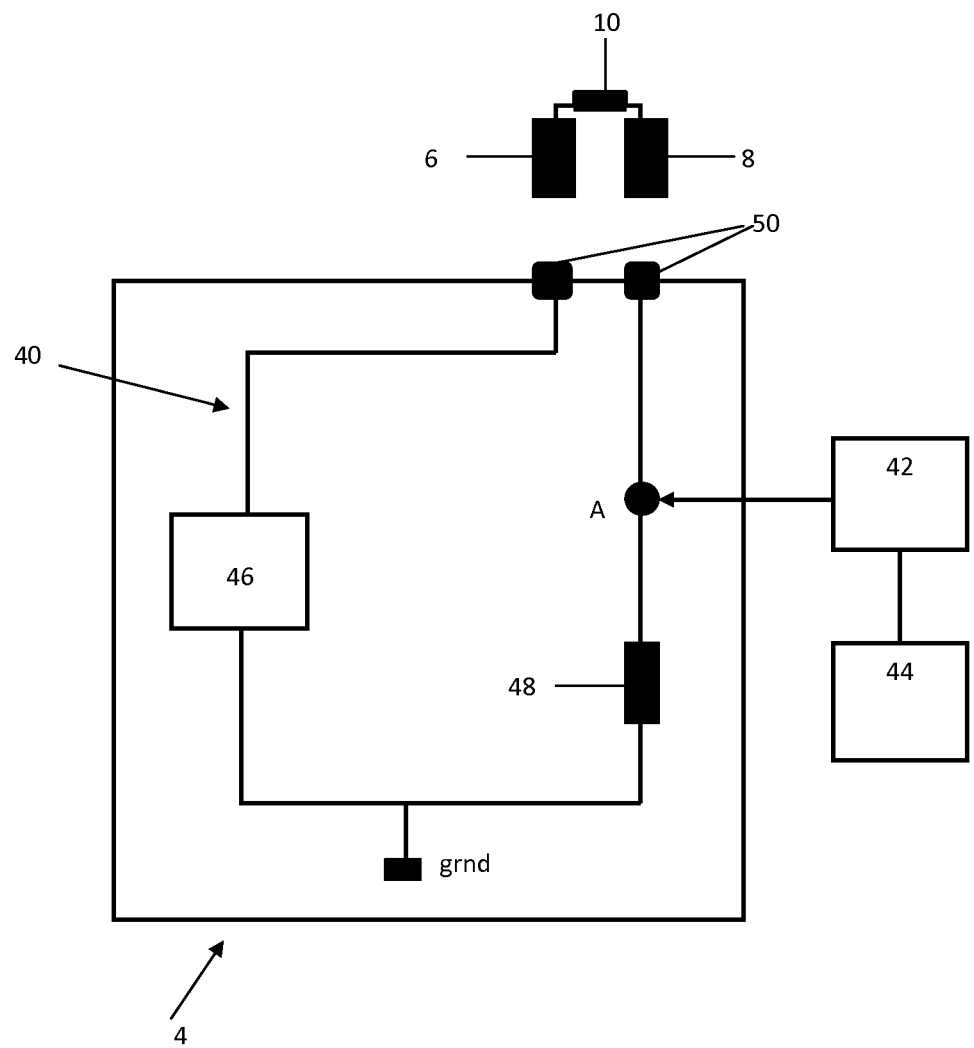

An embodiment of the invention will now be described by way of example only, with reference to the accompanying drawings, in which:

FIG. 1 is a schematic representation of an electrode identification system for use with an electrode suitable for children, and FIG. 2 is a schematic representation of an electrode identification unit for use with the electrode identification system of FIG. 1.

Referring to FIG. 1, the electrode identification system 1 comprises an electrode plug 2, a defibrillator socket 3 and an electrode identification unit 4.

The electrode plug 2 comprises a first pair of conducting contacts in the form of pins, 6, 8, an identification element in the form of a resistive identification element 10, a second pair of conducting contacts in the form of pins, 12, 14, a housing 16 having separate first and second cavity portions 18, 20 and an aperture (not shown). The housing is substantially rigid and is made of non conductive plastic. The first pair of conducting pins, 6, 8 and the resistive identification element 10 are moulded into the housing providing the first cavity portion 18. The second pair of conducting pins, 12, 14 are moulded into the housing providing the second cavity portion 20. The first and second cavity portions 18, 20 are separate from each other and hence the first pair of conducting pins, 6, 8 and the resistive identification element 10 are electrically separated from the second pair of conducting pins, 12, 14. The resistive identification element 10 is connected between first ends of the first pair of conducting pins, 6, 8. An electrode (not shown) is connected between first ends of the second pair of conducting pins, 12, 14. Second ends of the first pair of conducting pins, 6, 8 and the second pair of conducting pins, 12, 14 extend through the aperture of the housing 16.

In this embodiment, the electrode connected between first ends of the second pair of conducting pins, 12, 14 is a category of electrode for use with children. This category of electrode is associated with an identification characteristic of the resistive identification element 10 comprising a value of the resistance of the resistive identification element 10. In this embodiment, the value of the resistance is 10 kΩ. It will be appreciated that in another embodiment, the electrode connected between first ends of the second pair of conducting pins, 12, 14 could have a different category and a different associated identification characteristic of the identification element or a different associated value or range of values of the identification characteristic of the identification element of the electrode plug of the electrode. The important aspect is that the identification element presents a different identification characteristic or different identification characteristic value or range of values for each category of the possible different electrodes connectable to the defibrillator.

The defibrillator socket 3 comprises a first pair of conducting contacts in the form of pins, 24, 26, a second pair of conducting contacts in the form of pins, 28, 30, a housing 32 having separate first and second cavity portions 34, 36 and an aperture (not shown). The housing 32 is again substantially rigid and is made of non conductive plastic. The first pair of conducting pins, 24, 26 are moulded into the housing 32 providing the first cavity portion 34. The second pair of conducting pins, 28, 30 are moulded into the housing 32 providing the second cavity portion 36. The first and second cavity portions 34, 36 are separate from each other and hence the first pair of conducting pins, 24, 26 is electrically separated from the second pair of conducting pins, 28, 30. First ends of the first pair of conducting pins, 24, 26 and the second pair of conducting pins, 28, 30 extend through the aperture of the housing 32.

The electrode identification unit 4 is connected between second ends of the first pair of conducting pins, 24, 26. Second ends of the second pair of conducting pins, 28, 30 are connected to a defibrillator (not shown), by, in this embodiment, the defibrillator socket 3 being provided as an integral part of the defibrillator.

Referring to FIG. 2, the electrode identification unit 4 comprises a circuit 40, a signal detector 42 connected to the circuit 40, and a processor 44 connected to the signal detector 42. The circuit 40 is a voltage divider circuit comprising a DC voltage generator 46, a resistive electrical impedance element 48 having a resistance of 10 kΩ, and contacts 50. The contacts 50 connect to the first pair of conducting pins 6, 8 and the resistive identification element 10 of the electrode plug 2, via the first pair of conducting pins of the defibrillator socket (not shown). The arrangement of the circuit 40 and the resistive identification element 10 of the electrode plug is such that the voltage of the DC voltage generator 46 is divided between the resistive identification element 10 of the electrode plug 2 and the resistive electrical impedance element 48 of the voltage divider circuit 40.

In use of the electrode identification system 1, the electrode plug 2 is connected with the defibrillator socket 3, such that second ends of the first pair of conducting pins, 6, 8, of the electrode plug 2 make electrical contact with first ends of the first pair of conducting pins, 24, 26, of the defibrillator socket 3. Second ends of the second pair of conducting pins, 12, 14, of the electrode plug 2 also make electrical contact with first ends of the second pair of conducting pins, 28, 30, of the defibrillator socket 3. A circuit is formed between pin 24 of the defibrillator socket 3, pin 6, resistive identification element 10 and pin 8 of the electrode plug 2 and pin 26 of the defibrillator socket 3. Pins 24, 26 of the defibrillator socket 3 are connected to contacts 50 of the voltage divider circuit 40 of the electrode identification unit 4. The DC voltage generator 46 of the circuit 40 is operated and a signal is caused to flow around the circuit 40 and through the resistive identification element 10 of the electrode plug 2. The signal detector 42 detects the signal at point A of the circuit 40. The signal, or a measure of the signal, is passed to the processor 44, connected to the signal detector 42. The processor 44 uses the received signal along with the known voltage generated by the voltage generator 46 and the known resistance of the resistive electrical impedance element 48 of the voltage divider circuit 40 to determine the resistance of the resistive identification element 10 of the electrode plug 2, and to therefore identify the category of the electrode connected to the electrode plug 2 as a category of electrode for use with a child. The defibrillator is then able to generate and send appropriate child defibrillation signals via pins 28, 30 of the defibrillator socket 3 and pins 12, 14 of the electrode plug 2 to the electrode.

It will be appreciated that the identification element of the electrode plug may comprise any of a resistive identification element, a capacitive identification element, an inductive identification element. When the identification element of the electrode plug comprises a resistive identification element, the electrical impedance element of the voltage divider circuit may comprise a resistive electrical impedance element and the voltage generator of the voltage divider circuit may comprise a DC voltage generator. When the identification element of the electrode plug comprises a capacitive identification element, the electrical impedance element of the voltage divider circuit may comprise a capacitive electrical impedance element and the voltage generator of the voltage divider circuit may comprise an AC voltage generator. When the identification element of the electrode plug comprises an inductive identification element, the electrical impedance element of the voltage divider circuit may comprise an inductive electrical impedance element and the voltage generator of the voltage divider circuit may comprise an AC voltage generator.

The invention claimed is:

1. An electrode identification system for defibrillators, comprising:
   an electrode plug configured for connection to at least one electrode, the electrode plug comprising:
      a first pair of conducting contacts;
      an identification element connected between the first pair of conducting contacts, wherein the identification element comprises a resistor having a resistance value that identifies a type of the at least one electrode;
      a second pair of conducting contacts, distinct from the first pair of conducting contacts, configured for connection to the at least one electrode; and
      an electrode plug housing, the electrode plug housing encasing:
         the first pair of conducting contacts;
         the second pair of conducting contacts; and
         the identification element,
         wherein the electrode plug housing comprises a first aperture through which ends of the first pair of conducting contacts and the second pair of conducting contacts extend;
   a defibrillator socket configured for connection to a defibrillator and configured for connection to the electrode plug, the defibrillator socket comprising:
      a third pair of conducting contacts configured for connection to the first pair of conducting contacts of the electrode plug;
      a fourth pair of conducting contacts, distinct from the third pair of conducting contacts, configured for connection to the second pair of conducting contacts of the electrode plug and configured for connection to the defibrillator; and
      a defibrillator socket housing containing the third pair of conducting contacts, the fourth pair of conducting contacts, and a second aperture through which ends of the third pair of conducting contacts, the fourth pair of conducting contacts extend; and
   an electrode identification unit configured for connection to the defibrillator socket, the electrode identification unit comprising:
      a circuit comprising contacts for connection to the first pair of conducting contacts of the electrode plug via the third pair of conducting contacts of the defibrillator socket;
      a signal detector connected to the circuit configured to detect a signal from the identification element of the electrode plug; and
      a processor configured to:
         determine an identification characteristic of the identification element of the electrode plug based on the signal; and
         identify, based on the identification characteristic, a category of the at least one electrode connected to the electrode plug.

2. The electrode identification system of claim 1, wherein the defibrillator socket is configured for connection to a plurality of different categories of electrodes, and
   wherein the plurality of different categories of electrodes are each associated with one of a different identification characteristic, a different identification value, and a different range of identification values describing electrode plugs connected to the electrodes.

3. The electrode identification system of claim 2, wherein at least two types of electrode categories in the plurality of different categories of electrodes have identification elements having a distinction greater than a measurement accuracy of the electrode identification unit.

4. The electrode identification system of claim 2, in which the plurality of different categories of electrodes may comprise any one of a category of electrode for use with a child, a category of electrode for use with an adult, a category of electrode for measuring an ECG signal and not for delivering defibrillation signals, a category of size of the electrode, a category of shape of the electrode, a category of manufacture date of the electrode, a category of lot number of the electrode, a category of construction of the electrode.

5. The electrode identification system of claim 1, wherein the resistance value comprises a range of values of resistance to identify the type of the at least one electrode.

6. The electrode identification system of claim 1, wherein the identification element further comprises a capacitive identification element and the identification characteristic of the capacitive identification element comprises one of a value and a range of values of capacitance of the capacitive identification element.

7. The electrode identification system of claim 1, wherein the identification element further comprises an inductive identification element and the identification characteristic of the inductive identification element comprises one of a value and a range of values of inductance of the inductive identification element.

8. The electrode identification system of claim 1, wherein the first pair of conducting contacts and the second pair of conducting contacts of the electrode plug comprise pins, are elongate, and comprise a conductive element from a list comprising at least one of copper, gold, nickel, and tin.

9. The electrode identification system of claim 1, wherein the electrode plug housing is rigid and comprises a non-conductive plastic material from a list comprising at least one of Acrylonitrile butadiene styrene (ABS), polycarbonate, and compressed polystyrene.

10. The electrode identification system of claim 1, wherein the electrode plug housing encases a cavity divided into a first portion separated from a second portion.

11. The electrode identification system of claim 1, wherein
the electrode plug housing encases a cavity divided into a first portion separate from a second portion;
the first portion encases the first pair of conducting contacts and the identification element; and
the second portion encases the second pair of conducting contacts, thereby electrically insulating the first pair of conducting contacts and the identification element from the second pair of conducting contacts.

12. The electrode identification system of claim 1, wherein:
the electrode plug housing encases a cavity divided into a first portion separate from a second portion;
the first portion encases the first pair of conducting contacts and the identification element;
the second portion encases the second pair of conducting contacts, thereby electrically insulating the first pair of conducting contacts and the identification element from the second pair of conducting contacts; and
the first pair of conducting contacts and the identification element are moulded into the first portion of the cavity.

13. The electrode identification system of claim 1, wherein:
the electrode plug housing encases a cavity divided into a first portion separate from a second portion;
the first portion encases the first pair of conducting contacts and the identification element;
the second portion encases the second pair of conducting contacts, thereby electrically insulating the first pair of conducting contacts and the identification element from the second pair of conducting contacts;
the first pair of conducting contacts and the identification element are moulded into the first portion of the cavity; and
the second pair of conducting contacts are moulded into the second portion of the cavity.

14. The electrode identification system of claim 1, wherein the third pair of conducting contacts and the fourth pair of conducting contacts of the defibrillator socket comprise pins, are elongate, and comprise at least one of a conductive element from a list comprising copper, gold, nickel, tin, and any combination thereof.

15. The electrode identification system of claim 1, wherein the defibrillator socket housing is rigid and comprised of a non-conductive plastic material from a list comprising at least one of Acrylonitrile butadiene styrene (ABS), polycarbonate, and compressed polystyrene.

16. The electrode identification system of claim 1, wherein the defibrillator socket housing encases a cavity divided into a first portion separate from a second portion.

17. The electrode identification system of claim 1, wherein the defibrillator socket housing encases a cavity divided into a first portion separate from a second portion, the first portion encasing the third pair of conducting contacts and the second portion encasing the fourth pair of conducting contacts, thereby electrically insulating the third pair of conducting contacts and the fourth pair of conducting contacts from each other.

18. The electrode identification system of claim 1, wherein:
the defibrillator socket housing encases a cavity divided into a first portion separate from a second portion;
the first portion encases the third pair of conducting contacts; wherein
the second portion contains the fourth pair of conducting contacts, thereby electrically insulating the third pair of conducting contacts and the fourth pair of conducting contacts from each other; and
the third pair of conducting contacts are moulded into the first portion of the cavity.

19. The electrode identification system of claim 1, wherein:
the defibrillator socket housing encases a cavity divided into a first portion separate from a second portion;
the first portion encases the third pair of conducting contacts;
the second portion encases the fourth pair of conducting contacts, thereby electrically insulating the third pair of conducting contacts and the fourth pair of conducting contacts from each other;
the third pair of conducting contacts are moulded into the first portion of the cavity; and
the fourth pair of conducting contacts are moulded into the second portion of the cavity.

20. The electrode identification system of claim 1, wherein the circuit of the electrode identification unit is a voltage divider circuit comprising a voltage generator and an electrical impedance element.

21. The electrode identification system of claim 1, wherein:
the circuit of the electrode identification unit is a voltage divider circuit comprising an electrical impedance element and a voltage generator; and
the voltage divider circuit is connected to the first pair of conducting contacts of the electrode plug via the third pair of conducting contacts of the defibrillator socket in an arrangement which divides voltage of the voltage generator between the identification element of the electrode plug and the electrical impedance element of the voltage divider circuit.

22. The electrode identification system of claim 1, wherein:
   the circuit of the electrode identification unit is a voltage divider circuit comprising an electrical impedance element and a voltage generator; and
   the signal comprises a voltage.

23. The electrode identification system of claim 1, wherein:
   the circuit of the electrode identification unit is a voltage divider circuit comprising an electrical impedance element and a voltage generator; and
   the voltage divider circuit is connected to the first pair of conducting contacts of the electrode plug via the third pair of conducting contacts of the defibrillator socket in an arrangement which divides voltage of the voltage generator between the identification element of the electrode plug and the electrical impedance element of the voltage divider circuit.

24. A system comprising:
   an electrode unit, comprising:
      a pair of conducting contacts; and
      a cavity which encases the pair of conducting contacts and an identification element connected between the first pair of conducting contacts, the identification element comprising a resistor having a resistance value that identifies a type of electrode associated with the electrode unit; and
   a processor configured to perform operations comprising:
      receiving a voltage signal from a first connection to the electrode unit, wherein the voltage signal is based in part on the identification element in the electrode unit;
      determining, based on the voltage signal, the type of electrode associated with the electrode unit;
      determining, based on the type of electrode associated with the electrode unit, a defibrillation voltage to output; and
      causing a defibrillation voltage to be output via a second connection to the electrode unit, the second connection being distinct from the first connection, wherein the defibrillation voltage is based on the type of electrode.

25. An electrode unit, comprising:
   a pair of electrodes configured for defibrillation of a human patient;
   a pair of conducting contacts;
   an encased identification element comprising a resistor having a resistance value that identifies a type of electrode associated with the electrode unit, the encased identification element being encased in a cavity of the electrode unit;
   an encased identification element contact pair configured to complete a circuit comprising the encased identification element, the encased identification element being located between the encased identification element contact pair, the encased identification element contact pair being encased in the cavity; and
   a pair of electrodes contact pair, configured to convey a defibrillation voltage to a patient from a defibrillator via the pair of electrodes, the defibrillation voltage being determined based on the encased identification element.

* * * * *